(12) United States Patent
Sahley

(10) Patent No.: US 11,911,528 B2
(45) Date of Patent: Feb. 27, 2024

(54) HELMET CLEANING, SANITATION, AND DISPENSING SYSTEM

(71) Applicant: Joshua Sahley, New York, NY (US)

(72) Inventor: Joshua Sahley, New York, NY (US)

(*) Notice: Subject to any disclaimer, the term of this patent is extended or adjusted under 35 U.S.C. 154(b) by 151 days.

(21) Appl. No.: 17/480,096

(22) Filed: Sep. 20, 2021

(65) Prior Publication Data

US 2022/0001055 A1 Jan. 6, 2022

Related U.S. Application Data

(63) Continuation-in-part of application No. 16/020,165, filed on Jun. 27, 2018, now abandoned.

(Continued)

(51) Int. Cl.
*A61L 2/10* (2006.01)
*A61L 2/07* (2006.01)
(Continued)

(52) U.S. Cl.
CPC ........ *A61L 2/10* (2013.01); *A61L 2/07* (2013.01); *B08B 1/002* (2013.01); *B08B 1/006* (2013.01);
(Continued)

(58) Field of Classification Search
CPC .......... A61L 2/10; A61L 2/07; A61L 2202/11; B08B 1/002; B08B 1/006; B08B 1/04;
(Continued)

(56) References Cited

U.S. PATENT DOCUMENTS 5,369,892 A ‡ 12/1994 Dhaemers ............... D06F 58/10
34/224
5,807,521 A * 9/1998 Franetzki ................. A61L 2/07
422/128

(Continued)

FOREIGN PATENT DOCUMENTS

CN 113192724 A * 7/2021 ............. B01D 46/10
DE 102017112001 A1 * 12/2018 ........... A46B 13/001

(Continued)

OTHER PUBLICATIONS

Bike helmet vending machines study in Boston by Susi Jul. 20, 2013; velojoy.‡

(Continued)

*Primary Examiner* — Stephen M Gravini
(74) *Attorney, Agent, or Firm* — White-Welker & Welker, LLC; Matthew T. Welker, Esq.

(57) ABSTRACT

A helmet rental system keeping the helmets in individual boxes that have a self-cleaning system built into the system to make the helmets safe for reuse. The full surface of the helmet is to be exposed to heat, possible steam, cleaner, one or more rotating brush(es) and/or UV light to clean the surface fully. The helmet holder allows the heat, steam, cleaner, brushes, and light to easily hit the surface. The cleaning system is based on heat and then cool off the box with AC and/or vent system before allowing the helmet to be rented again after each return. Heat comes from vents under the helmet holding system, holding it in place and/or from all around the helmet. Boxes are modular so one could simply remove a few screws to add or remove rows or boxes to the system to expand or reduce the amount of available helmets and configuration.

16 Claims, 8 Drawing Sheets

Related U.S. Application Data

(60) Provisional application No. 62/525,784, filed on Jun. 28, 2017.

(51) Int. Cl.
    *B08B 1/00*     (2006.01)
    *B08B 1/04*     (2006.01)
    *B08B 3/00*     (2006.01)
    *B08B 13/00*     (2006.01)
    *G06Q 30/0645*     (2023.01)
    *H02S 99/00*     (2014.01)
    *H04L 65/61*     (2022.01)

(52) U.S. Cl.
    CPC ................ *B08B 1/04* (2013.01); *B08B 3/00* (2013.01); *B08B 13/00* (2013.01); *G06Q 30/0645* (2013.01); *A61L 2202/11* (2013.01); *B08B 2230/01* (2013.01); *H02S 99/00* (2013.01); *H04L 65/61* (2022.05)

(58) Field of Classification Search
    CPC ....... B08B 3/00; B08B 12/00; B08B 2230/01; G06Q 30/0645; G07F 17/042; G07F 9/105; H04L 65/61; H02S 99/00; A63B 1/0045; A63B 1/00; A42B 3/06; A42B 3/00; F26B 5/00; F26B 3/00; F26B 21/06; F26B 21/00
    USPC ............................................................. 34/90
    See application file for complete search history.

(56) References Cited

U.S. PATENT DOCUMENTS

| | | | | |
|---|---|---|---|---|
| 8,336,113 | B2 ‡ | 12/2012 | Uttrachi | A61F 9/067 |
| | | | | 2/8.6 |
| 8,496,308 | B2 ‡ | 7/2013 | Zabbatino | G06Q 30/0645 |
| | | | | 312/407 |
| 8,597,588 | B1 * | 12/2013 | Trabalka | A61L 2/10 |
| | | | | 250/455.11 |
| 9,418,503 | B2 ‡ | 8/2016 | Williams | B29C 64/25 |
| 9,867,510 | B2 ‡ | 1/2018 | Bethel | G08B 25/016 |
| 10,559,147 | B2 ‡ | 2/2020 | Homad | H04W 4/35 |
| 10,894,100 | B2 * | 1/2021 | Georgeson | B08B 5/02 |
| D981,662 | S * | 3/2023 | Georgeson | D32/1 |
| 2004/0101456 | A1 ‡ | 5/2004 | Kuroshima | A61B 50/13 |
| | | | | 422/297 |
| 2011/0025181 | A1 ‡ | 2/2011 | Vinke | A47B 67/04 |
| | | | | 312/257.1 |
| 2011/0074256 | A1 ‡ | 3/2011 | Boice | A47B 81/00 |
| | | | | 312/213 |
| 2013/0199581 | A1 ‡ | 8/2013 | Christopherson | B08B 7/04 |
| | | | | 134/103.2 |
| 2014/0379124 | A1 ‡ | 12/2014 | Dallaire | G07F 17/0057 |
| | | | | 700/237 |
| 2017/0290726 | A1 ‡ | 10/2017 | Hovenden | A47B 81/00 |
| 2018/0094855 | A1 ‡ | 4/2018 | Allen | F26B 21/001 |
| 2019/0000172 | A1 ‡ | 1/2019 | Sahley | A63B 71/0045 |
| 2022/0001055 | A1 * | 1/2022 | Sahley | G06Q 30/0645 |
| 2023/0123589 | A1 * | 4/2023 | Storey | A01N 59/00 |
| | | | | 422/28 |

FOREIGN PATENT DOCUMENTS

| | | | | |
|---|---|---|---|---|
| EP | 1566185 | A4 ‡ | 9/2007 | ............. A61B 50/18 |
| FR | 2714348 | A1 ‡ | 6/1995 | ............... B62H 3/00 |
| WO | WO-2004047876 | A1 ‡ | 6/2004 | ............... A61L 2/07 |
| WO | WO-2005013212 | A2 ‡ | 2/2005 | ............. G07F 11/00 |

OTHER PUBLICATIONS

A Vending Machine Serves Up Safety, by Eric Moskowitz, Dec. 31, 2011; Boston Globe.‡

\* cited by examiner
‡ imported from a related application

HELMET CLEANING, SANITATION, AND DISPENSING SYSTEM

TECHNICAL FIELD OF THE INVENTION

The present invention relates in general to a cleaning, sanitation and dispensing system. More specifically, the present invention relates to a helmet cleaning, sanitization and dispensing system. As taught by the present invention, the full surface of the helmet is to be exposed to heat, possible steam, cleaner, one or more rotating brush(es) and/or UV light to clean the surface fully. The helmet holder allows the heat, steam, cleaner, brushes, and light to easily hit the surface.

BACKGROUND OF THE INVENTION

The average careful bike rider may still crash about every 4,500 miles. Head injuries cause 75% of our nearly 700 annual bicycle deaths. Medical research shows that bike helmets reduce or prevent most of cyclists' head injuries. And helmets may be required by law in your area.

A helmet reduces the peak energy of a sharp impact. This requires a layer of stiff foam to cushion the blow. Most bicycle helmets use crushable expanded polystyrene (EPS), the picnic cooler foam. It works well, but when crushed it does not recover. Expanded polypropylene (EPP) foam does recover, but is much less common. Collapsible plastic liner materials recently appeared and offer promise. The spongy foam pads inside a helmet are for comfort and fit, not for impact protection.

The helmet must stay on your head even when you hit more than once—usually a car first, and then the road, or perhaps several trees on a mountainside. So it needs a strong strap and buckle. The helmet should sit level on your head and cover as much as possible. Above all, with the strap fastened you should not be able to get the helmet off your head by any combination of pulling or twisting. If it comes off or slips enough to leave large areas of your head unprotected, adjust the straps again or try another helmet. Keep the strap comfortably snug when riding. The straps hold your helmet on, not the rear stabilizer.

Most bike helmets are made of EPS foam with a thin plastic shell. The shell helps the helmet skid easily on rough pavement to avoid jerking your neck. The shell also holds the foam together after the first impact. Some excellent helmets are made by molding foam in the shell rather than adding the shell later.

The biggest obstacles to providing helmets are hygiene, cost, and liability. Most bike share programs in the U.S. encourage riders to use their own helmets, partnering with sponsors to offer big discounts or even give them away. But that means carrying the bulky headgear around. What is needed is a method for dispensing and collecting helmets, cleaning them so they are hygienic, and re-distributing them in a manner that is cost effective.

Seattle and Boston have found ways around some of these problems. Each is installing helmet vending machines that work just like the bike technology itself. With the swipe of a credit card, a helmet will be available on demand along with the bikes. Riders return the helmets to collection bins, where they are picked up each day, taken to a warehouse, cleaned and inspected before they can be used again.

The shortcoming with these prior art systems is that they are not cost effective nor are they a "green" solution. In the current prior art systems, the energy and man power to continually transport, clean, and distribute helmets is tremendous and lacks any cost efficiently. Additionally, the transportation necessary to collect and return helmets causes additional pollution and traffic congestion, which is one reason many cities encourage biking.

What is needed is a helmet dispensing solution that provides usage tracking, collection and dispensing, in addition to a cleaning system and means for removing damaged helmets from the system.

SUMMARY OF THE INVENTION

The present invention is a helmet rental system designed to be easy to use for customers by keeping the helmets in individual boxes that have a self-cleaning system built into the system to make the helmets safe for reuse.

The focus of the main invention, and one aspect of the present invention which makes it novel and non-obvious focuses on the cleaning mechanism and the unique design that allows for the full surface of the helmet to be exposed to heat, possibly steam, cleaner, one or more rotating brush (es), and/or UV light to clean the surface fully.

In an alternative version of the present invention, poles which would allow a helmet to slide on that suspends the helmet in air inside the same box so it keeps the helmet hovering over the Heat, UV light, or any other cleaning lights and possibly steam and/or cleaner agent are used.

The present invention is differentiated from the prior art in how it exposes the full surface of the helmet allowing for cleaning. Prior art systems that include stacking helmets would make this impossible. The approach of the present invention allows any current cleaning options and future cleaning options to be applied inside this box by using this approach. The modular case allows for unique shapes and easy replacement of the individual cleaning boxes if anything breaks inside, not requiring the full case to be fixed if any of the individual helmet cleaner modulars break.

In alternative embodiments, the present invention teaches flexibility and whether each box has its own individual heating system or if they are broken into rows with a unit for each row or just one large system that allows the air into the individual boxes with opening and closing flaps.

The cleaning system could be based on heat that reaches a high enough temperature, around 130 degrees, for approximately 4-8 minutes and then cool off the box with AC and/or vent system for a few minutes before allowing the helmet to be rented again after each return.

The heat could come from vents under the helmet holding system, holding it in place and/or from all around the helmet.

As taught by the present invention, the full surface of the helmet is to be exposed to heat, possible steam, cleaner, one or more rotating brush(es) and/or UV light to clean the surface fully. The helmet holder allows the heat, steam, cleaner, brushes, and light to easily hit the surface.

The individual boxes or rows of boxes could be modular so one could simply remove a few screws and remove a box to replace it with its own heat system attached or just replace the helmet holder insert, door, etc. One can also add or remove rows or boxes to the system to expand or reduce the amount of available helmets.

The base station 101 can be expanded upon, shrank down or adjusted to any custom size based on the cube stacking and connecting of the individual boxes 102. The base station 101 can also be individual boxes 102 or an elevated row of boxes 106 built to fit around and/or right over existing bike racks for convenience and space saving as illustrated.

The system will possibly have solar panels to produce all or a portion of the electricity needed for the system.

Each box could also have UV lights to add additional sanitation as well as light up the box for viewing. One could also consider having individual plastic helmet caps, similar to a schooner cap that you can use to cover the inside of the helmet as extra protection. The present invention could use an all-natural or safe chemical spray dispenser to sanitize the helmet also if needed.

The box will have a damaged button to press when a helmet is returned damaged to signal that the helmet cannot be rented until serviced. This relies on the customers to signal that the helmet is damaged. Boxes will also be disabled by the system software if their heating or cooling system isn't working.

The helmet will experience wear and tear, so one will make the helmet have replaceable outer shells, inner support and/or straps. So, one can just refresh the helmets without replacing them every time one is damaged or worn out looking. The replaceable, thin outer shells could be custom printed for replaceable design concepts, seasonal themes or sponsor marketing (logo and color) themes.

The helmet will have open places for a marketing sponsor logo or logos on the sides of the helmet as well as a possible light system on the back and/or front that can light up in the shape of the sponsors logo for safety and high visibility marketing. The light system could also just be a simple small light as well as possible reflectors to add visibility.

The helmet may have a tracking system built into it running on low energy power that would track the helmets location and/or let the system keep track of returns/rentals and locations availability.

The helmet may have sensors on it that if the padding is damaged or if a certain amount of pressure or crack is recorded that an emergency call can be placed with location tracking. To make it more efficient, the sensor could send signal to your cell phone through Bluetooth (or a similar low energy connection type) and call 911 from our app or directly through the phone, possibly without the app. It could also signal your phone and have a Rep call the number to check before calling 911 and also they can check if the bike continues moving again or not to determine seriousness of accident.

An app could also be used to let customers know what station has available helmets for rent and time left on your rental.

The rental system would have a credit card reader as well as a simple yearly key card or fob that customers can keep on keychain, pocket or wallet that simply is swiped and a helmet box is assigned to them for fast rental service. May possibly require the card or fob for returns to assign a particular open box to return the helmet to or one will just let any open box be selected by the customers for faster returns.

The rental system station will have a video camera at the top to record transactions for safety.

The cooling system may be individual units per box or row or one larger unit that has controlled vents that let's air into the boxes after heating phase is over.

All the stations will be connected throughout the city keeping track of helmet locations, availability, and usage.

BRIEF DESCRIPTION OF THE DRAWINGS

The accompanying drawings, which are incorporated herein and form a part of the specification, illustrate the present invention and, together with the description, further explain the principles of the invention and to enable a person skilled in the pertinent art to make and use the invention.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figure, it is possible to see the various major elements constituting the apparatus of the present invention.

Figure 1:
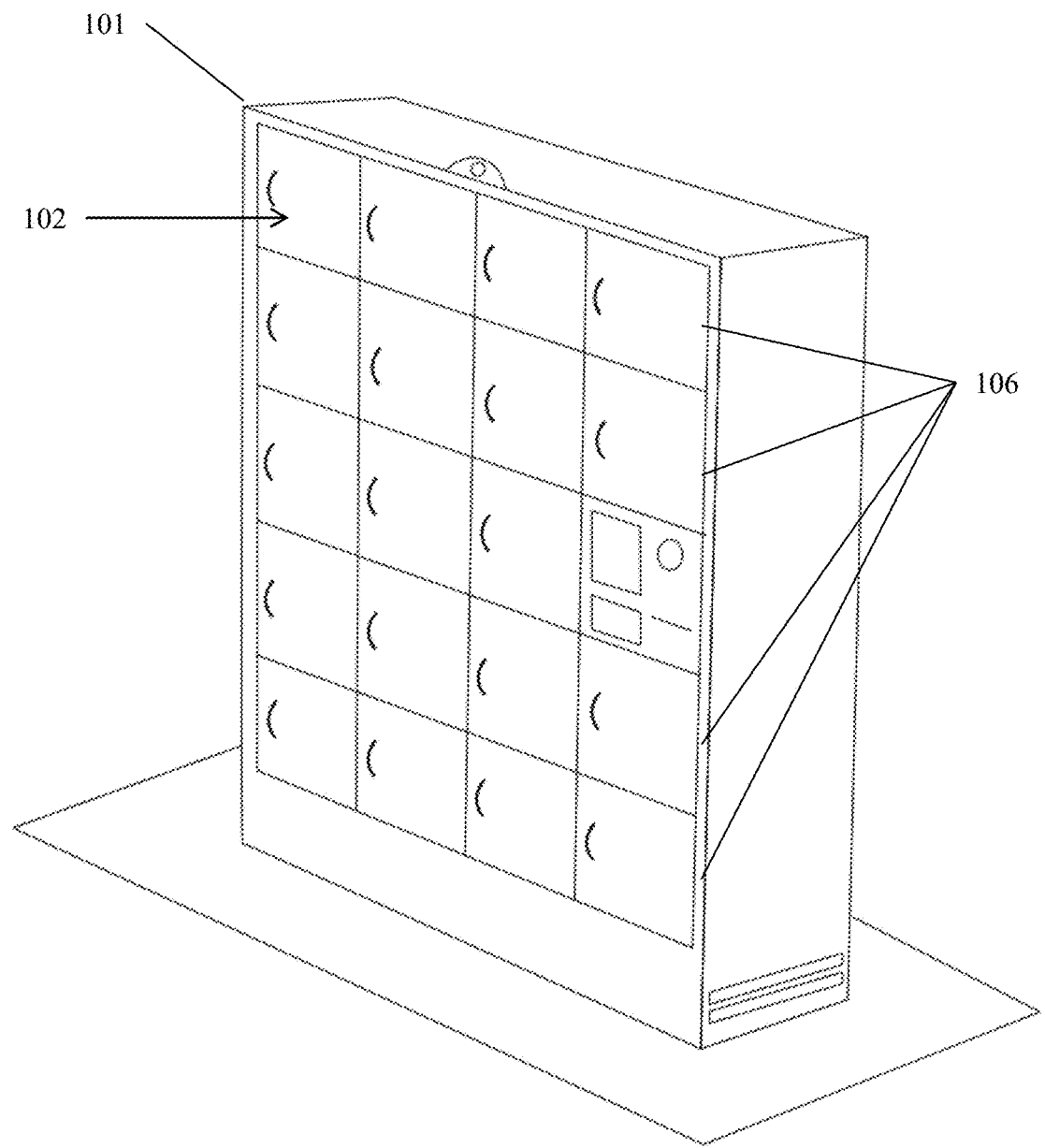
FIG. 1 illustrates a base station according to one embodiment of the present invention.

Now referring to FIG. 1 a base station 101 according to one embodiment of the present invention. The present invention is a helmet rental system designed to be easy to use for customers by keeping the helmets in individual boxes 102 that have a self-cleaning system built into the system to make the helmets 103 safe for reuse.

The cleaning system could be based on heat that reaches a high enough temperature, around 130 degrees, for approximately 4-8 minutes and then cool off the box 102 with AC and/or a vent system for a few minutes before allowing the helmet 103 to be rented again after each return.

The heat could come from vents under the helmet holding system, holding it in place and/or from all around the helmet 103. The system can use numerous individual and exchangeable heating units on the back of each box or larger units for each row or half of machine or possibly one large unit for the whole thing (but probably not).

In an alternative embodiment, besides just having heat, one of the options is to first blowout steam and then switch to just heat to dry a helmet. Then, possibly having regular air blow at the end to cool the helmet some to reduce cleaning time and increase turn over time for usage.

In still another embodiment, the use of steam being sprayed through the helmet holder at first and then switching off to finish the timed cleaning cycle with just strong heat for the required time to kill lice and other bacteria/germs.

In yet another alternative embodiment, an optional or additional cool down phase can be incorporated that allows cold air to blow into the boxes or possibly just a waiting phase at the end to let the heat dissipate.

At this stage, the inventor has determined through research and evaluation that numerous, exchangeable units would be preferable over a single larger unit for an entire system. This swap-ability of the module embodiment allows the updating and use of different heating technologies as they progress in addition to other advantages discussed in this specification.

Figure 7:
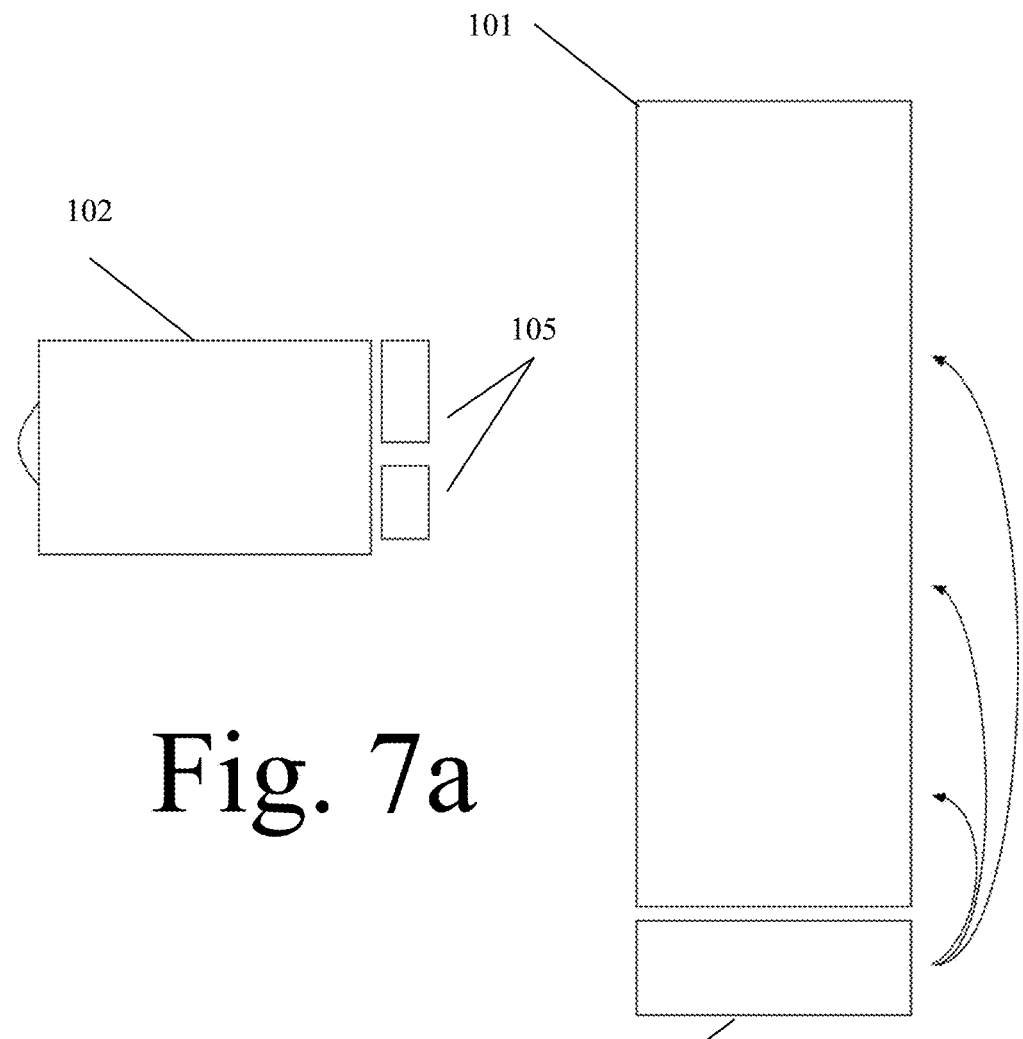
FIG. 7a illustrates a base station according to one embodiment of the present invention where each dispensing box has an individual cooling system.
FIG. 7b illustrates a base station according to one embodiment of the present invention where each dispensing unit has an individual cooling system at the base for servicing each box.

FIG. 7a illustrates a base station 101 according to one embodiment of the present invention where each dispensing box 102 has an individual cooling system 105.

FIG. 7b illustrates a base station 101 according to one embodiment of the present invention where each dispensing base station unit 101 has an individual cooling system 103 at the base of the base station 101 for servicing each box 102.

The individual boxes 102 or rows of boxes 106 could be modular so one could simply remove a few screws and remove a box 102 to replace it with its own heat system attached 103 or just replace the helmet holder insert 107, door, etc. One can also add or remove rows 106 or boxes 102 to the system to expand or reduce the amount of available helmets 103.

Figures 2A, 2B:
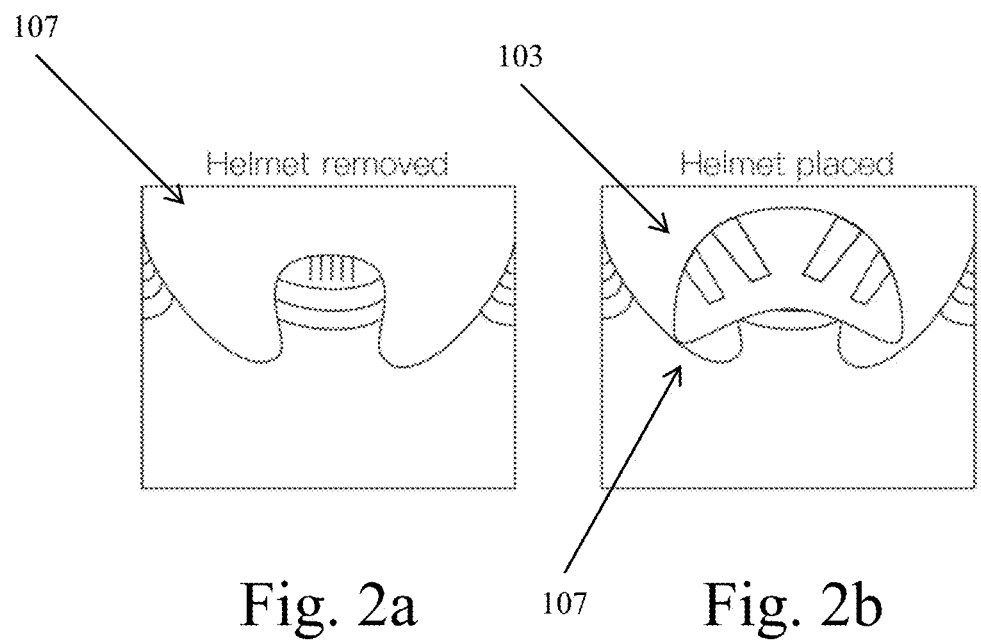
FIG. 2a illustrates the interior of a based station supporting module with the helmet removed showing the helmet pedestal.
FIG. 2b illustrates the interior of a based station supporting module with the helmet in pace on a helmet holder or pedestal.

FIG. 2a illustrates the interior of a based station supporting module with the helmet removed showing the helmet pedestal 107. FIG. 2b illustrates the interior of a based station supporting module with the helmet 103 in place on a helmet holder or pedestal 107. The helmet holder or pedestal 107 with the holes in it can be exchangeable and be different shapes to accommodate different helmet types and sizes if/as needed.

The system will possibly have solar panels to produce all or a portion of the electricity needed for the system.

Each box could also have UV lights to add additional sanitation as well as light up the box 102 for viewing.

In another embodiment, the present invention could also consider having individual plastic helmet caps, similar to a schooner cap, that you can use to cover the inside of the helmet as extra protection.

The present invention could use an all-natural or safe chemical spray dispenser to sanitize the helmet also if needed.

The box will have a damaged button 108 to press on a user interface 109 when a helmet is returned damaged to signal that the helmet cannot be rented until serviced. This relies on the customers to signal that the helmet is damaged.

Boxes 102 will also be disabled by the system software if their heating or cooling system 105 isn't working.

Figure 8:
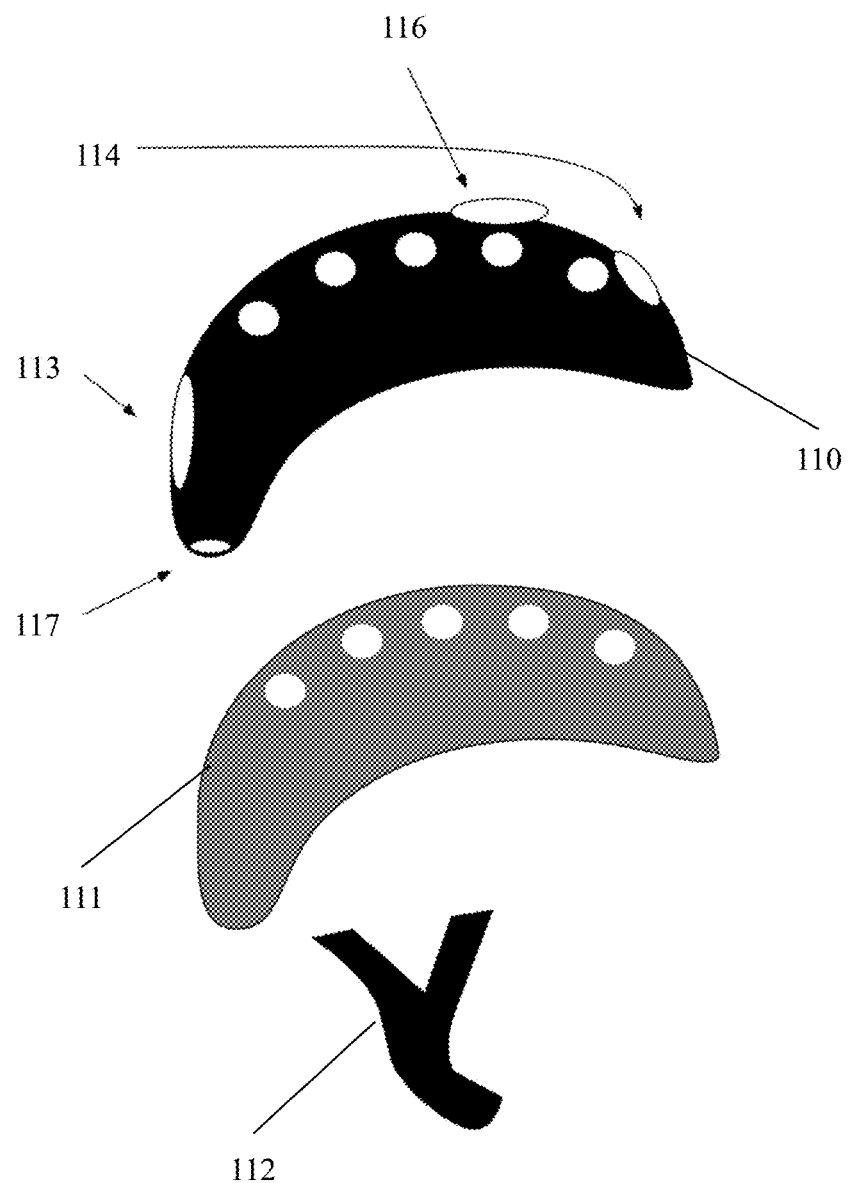
FIG. 8 illustrates a helmet design for use and integration with the vending system of the present invention.

FIG. 8 illustrates a helmet design for use and integration with the vending system of the present invention.

The helmet 103 will experience wear and tear, so the helmet will have replaceable outer shells 110, inner support 111 and/or straps 112. So, one can just refresh the helmets without replacing them every time one is damaged or worn out looking. The replaceable, thin outer shells 110 could be custom printed for replaceable design concepts, seasonal themes or sponsor marketing (logo and color) themes.

The helmet 103 will have open places for a marketing sponsor logo or logos on the sides of the helmet as well as a possible light system on the back 113 and/or front 114 that can light up in the shape of the sponsors logo for safety and high visibility marketing. The light system could also just be a simple small light as well as possible reflectors to add visibility.

The helmet 103 may have a tracking system 116 built into it running on low energy power that would track the helmets location and/or let the system keep track of returns/rentals and locations availability.

The helmet may have sensors 117 on it that if the padding is damaged or if a certain amount of pressure or crack is recorded that an emergency call can be placed with location tracking. To make it more efficient, the sensor could send signal to a user's cell phone through BLUETOOTH or a similar low energy connection type and call 911 from the software application or directly through the phone, possibly without the software application. The helmet 103 could also signal a user's phone and have a call placed to the user's number to check before calling 911 and also the system can check and determine if the bike continues moving again or not to determine seriousness of accident.

An software app or application could also be used to let customers know what station has available helmets for rent and time left on your rental.

The rental system would have a credit card reader as well as a simple yearly key card or fob that customers can keep on keychain, pocket or wallet that simply is swiped and a helmet box is assigned to them for fast rental service. May possibly require the card or fob for returns to assign a particular open box to return the helmet to or one will just let any open box be selected by the customers for faster returns.

The rental system station will have a video camera at the top to record transactions for safety.

The cooling system 105 may be individual units per box or row or one larger unit that has controlled vents that let's air into the boxes after heating phase is over. The present invention can be built in two configurations, a first having an individual heat and cooling system 105 on each box or just either heat or cooling and a second configuration where heat and cooling comes from a single system 118 from the base or a single system per row or column.

Figure 6:
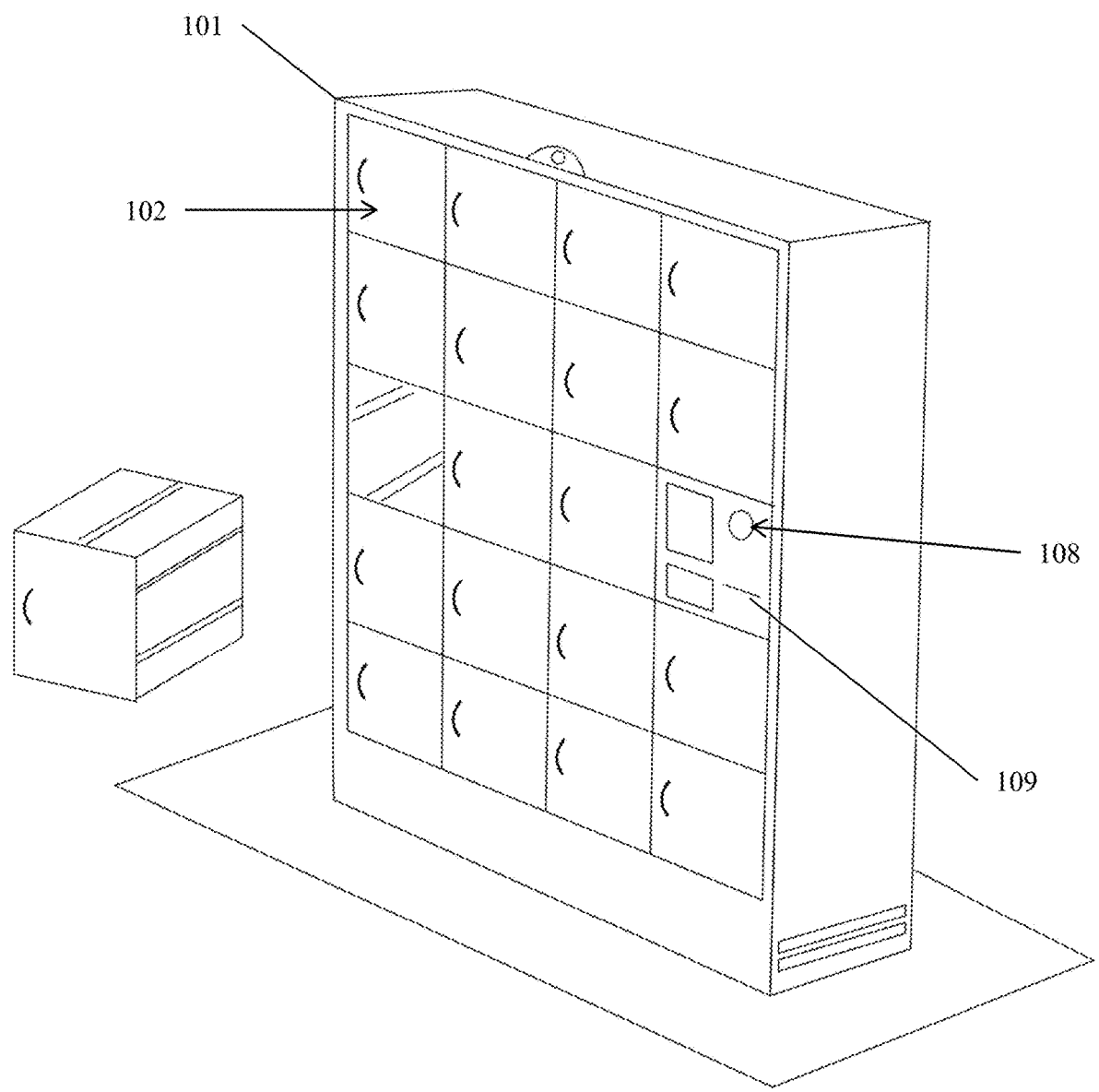
FIG. 6 illustrates a base station according to one embodiment of the present invention wherein the system can have removable boxes for easily repair and replacement.

FIG. 6 illustrates a base station 101 according to one embodiment of the present invention wherein the system can have removable boxes 102 for easily repair and replacement. The station base 101 is designed to be modular so boxes 102 or rows of boxes 106 can be removed, added or replaced. Giving the unit expansion capabilities over time as well as custom shapes. Ex: tall rectangle, box, long rectangle, long or tall row or unique shapes bade up by the boxes like L or U base shapes giving the present invention flexibility for space limitations.

For example, if the station base needs to go across a long wall or fit on a narrow sidewalk, etc. One could also have multiple bases that hookup wired or wirelessly to the main station so one only need one computer system (pay station) at that location but can have multiple bases forming a grid to help in dense areas.

All the stations will be connected throughout the city keeping track of helmet locations, availability, and usage.

Figure 3:
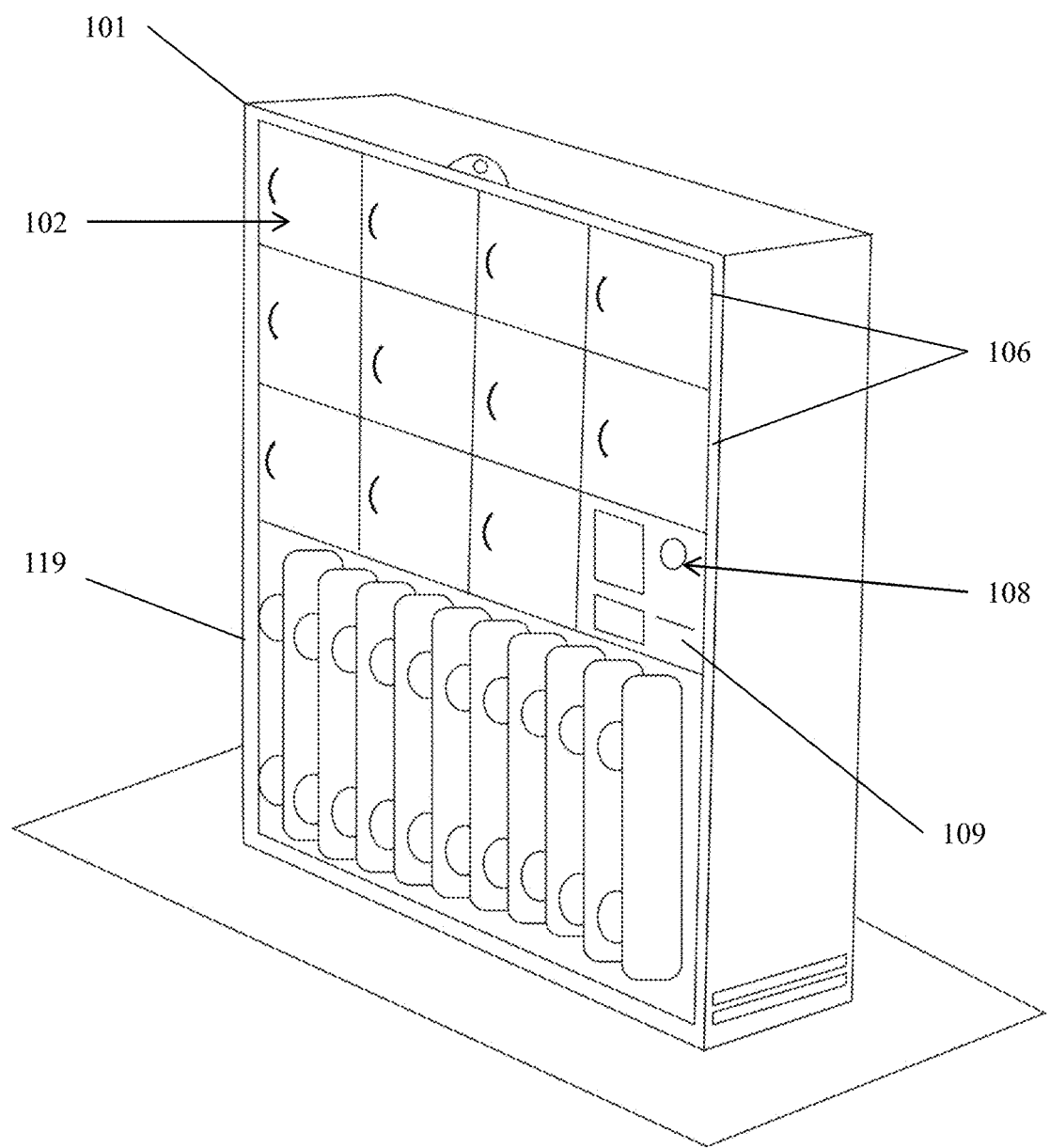
FIG. 3 is a helmet cleaning, sanitation, and dispensing system wherein the base station is combined with a skateboard rental system.
Figure 4:
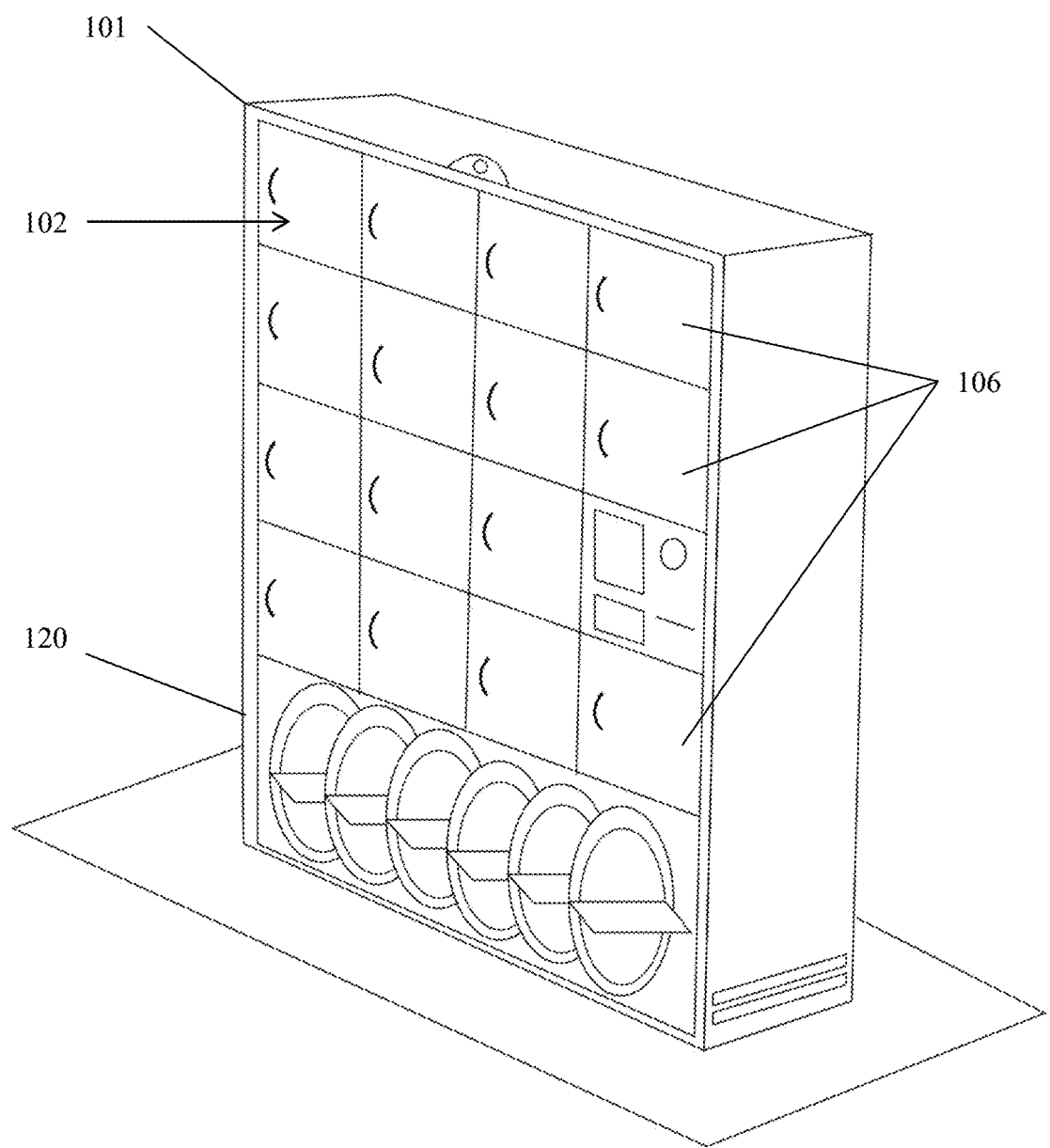
FIG. 4 is a helmet cleaning, sanitation, and dispensing system wherein the base station is combined with a single wheel gyroscope style electric scooter rental system.

The modular nature of the helmet cleaning, sanitation, and dispensing system of the present invention allows it to be combined with any number of transportation devices such as skateboards, bikes, unicycles, electric scooters, etc., that are typically stored or secured in "racks". FIG. 3 is a helmet cleaning, sanitation, and dispensing system wherein the base station 101 is combined with a skateboard rental system 119. FIG. 4 is a helmet cleaning, sanitation, and dispensing system wherein the base station 101 is combined with a single wheel gyroscope style electric scooter rental system 120.

For Example: the bike rack has a small box on top of the support for each bike. So, if a bike is rented, they can get access to the helmet box linked with that bike.

In still another embodiment, the base station could be modified to support a plurality of one wheel gyro scooters. A one wheel gyro scooter is super small and you put your feet on the left and right of a small wheel and they go like 15 mph. The rack could possibly have an expandable bottom row or two that could hold numerous of those for rent also. The station would charge them when they're returned.

Figure 5:
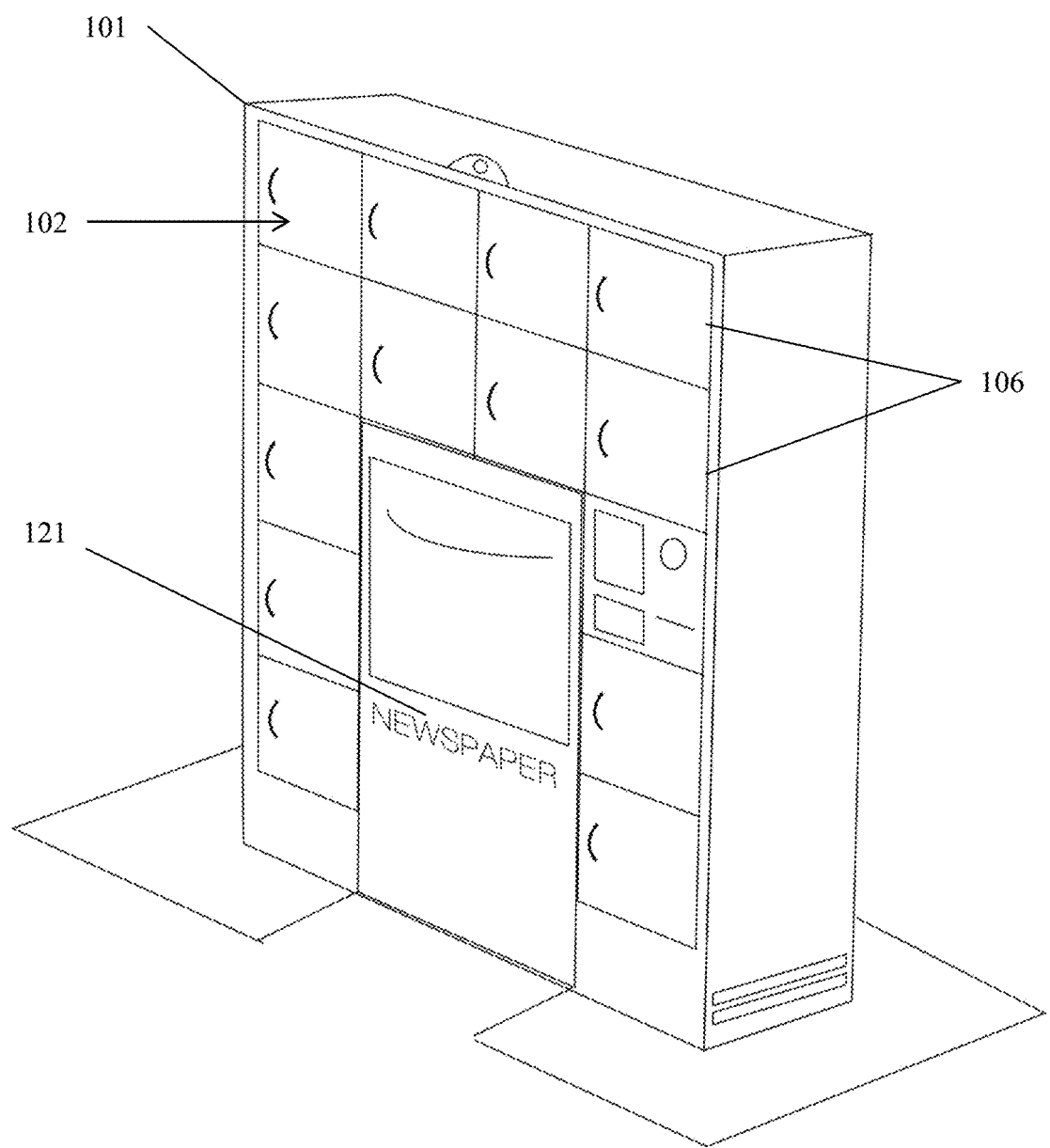
FIG. 5 illustrates the helmet dispending system and the modularity that allows it to be shaped to fit the environment, here around a newspaper dispensing machine.

FIG. 5 illustrates the helmet dispending system and the modularity that allows it to be shaped to fit the environment, here around a newspaper dispensing machine. In this embodiment, the modular helmet cleaning, sanitation, and dispensing system has its boxes arranged in such a manner to create a supporting structure that surrounds an existing object, here a newspaper dispenser 120, commonly found on street sidewalks.

The focus of the main invention, and one aspect of the present invention which makes it novel and non-obvious focuses on the cleaning mechanism and the unique design that allows for the full surface of the helmet to be exposed to heat, possibly steam, cleaner, one or more rotating brush (es), and/or UV light to clean the surface fully.

In an alternative version of the present invention, poles which would allow a helmet to slide on that suspends the helmet in air inside the same box so it keeps the helmet hovering over the Heat, UV light, or any other cleaning lights and possibly steam and/or cleaner agent are used.

The present invention is differentiated from the prior art in how it exposes the full surface of the helmet allowing for cleaning. Prior art systems that include stacking helmets would make this impossible. The approach of the present invention allows any current cleaning options and future cleaning options to be applied inside this box by using this approach. The modular case allows for unique shapes and easy replacement of the individual cleaning boxes if anything breaks inside, not requiring the full case to be fixed if any of the individual helmet cleaner modulars break.

In alternative embodiments, the present invention teaches flexibility and whether each box has its own individual heating system or if they are broken into rows with a unit for each row or just one large system that allows the air into the individual boxes with opening and closing flaps.

The custom shape of the system of the present invention allows it to have rentals of scooters or single wheel transportation devices in the same base if needed for convenience of space and rental ease, allowing people to rent both at the same time as illustrated.

In yet another embodiment, the modular boxes are separated more as well compared to those show in the figures so a user is shown one box at the top of every bike slot for future racks, so each biker gets a bike and a helmet linked together in this embodiment.

In another embodiment, the helmet locker could have a section or full machine of empty helmet lockers for people who own their personal helmet and want the convenience of storing it.

In another embodiment referred to as HELMETVIEW—a helmet geared for tourists with a built-in camera. It automatically starts recording when they put it on and when they return it the full video is uploaded to a server and sends you a link to download.

The boxes can be hardwired, connected through Wi-Fi or BLUETOOTH, depending on the configuration and distance from the bases computer location. With the built in BLUETOOTH speaker in the helmets and wifi connection to the base, the helmets can audibly remind users of time left, directions, site seeing routes and any warnings like weather or danger.

If the helmet has a battery and sensors around it, the helmet can provide a wearer with collision detection, blind spot sensors, etc. Also, the helmet can be provided with a clear eye shield in the front as glasses that could project augmented reality (AR) information on screen about tourist info based on proximity, warnings, or directions connected to the BLUETOOTH headset using phone's GPS or built in, etc.

The eye shield can have the ability to display directions, warnings and AR (Augmented Reality) to show points of interest for self-guided tours, shops/restaurants, GPS information, etc., while still allowing the user/wearer to see through the shield. The helmet may also provide the headphones for proximity information for tourists, directions, etc. using the sensors and/or phone.

The helmet may also provide one or more internal Bluetooth speakers that don't go in a wearer's ears to allow hearing outside sounds for safety. In this embodiment, the built in speakers in the helmet will probably be the way to go for tourist info, GPS, warnings, etc. It may say "on your left" or just beeps to warn a wearer. An initial commercial product would probably have this before the visor. To be clear the speaker system is a separate feature from the visor and clearly either hooks up or connects to a smart phone with BLUETOOTH or other wireless communication or has a built in system in the helmet, More than likely any commercial product will support a wireless connection to a smart phone.

The helmet may also be provided with a 360 degree motion sensor on top of helmet. The motion sensor can then warn a wearer with left or right side sounds in speaker or flash in corner of visor. The visor on a helmet can additionally display reminders, AR for things like paths, names of buildings displayed and directions.

Helmet sensors can notice speed and when drastically moving or slowing the light on helmet can light up brighter like a break light does. If impact happens and the helmet isn't moving, the lights around the helmet can flash to get attention as well as call 911 and give dispatcher access to camera view possibly.

Bikes or other rental transportation devices could have a BLUETOOTH lever mounted on handlebars to signal going left or right and lights on helmet could signal it.

Helmets could have plastic style caps similar to schooner caps that cover the inside of helmet but odds are that'll create heat and be uncomfortable.

Alternative means of cleaning and sanitation for the helmets could include a spray cleaner inside and out of helmet once placed in box instead of heat and then dried with forced air flow.

Another cleaning and sanitation solution could be the use of an outside spray cleaner with wipe dispenser that is activated with every rental for extra cleaning or instead of heat or spraying inside box.

Yet another cleaning and sanitation solution could be the use of peel-able and replaceable inside layers of the helmet. In this embodiment as user would grab a thin layer and peel off to remove/reveal a fresh layer of helmet protection. These layers would have to be replaced pretty often though and would create additional system costs and garbage/waste issues.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A helmet cleaning, sanitation, and dispensing system comprising:
   a base keeping a plurality of helmets in individual boxes that have a self-cleaning system built into the helmet cleaning, sanitation, and dispensing system to make the helmets safe for reuse;
   the base comprised of a plurality of individual boxes;
   a cleaning system;
      a cleaning system mechanism allowing for a full surface of a helmet to be exposed to heat, steam, cleaner, one or more rotating brush(es), and/or UV light to clean a surface fully; and
      a cooling system that may be individual units per box or row or one larger unit that has controlled vents that allows air into the boxes after a heating phase is over.

2. The helmet cleaning, sanitation, and dispensing system of claim 1, wherein
   the cleaning system is based on heat that reaches a temperature of 130 degrees Fahrenheit, for approximately 4-8 minutes and then cool off a box with air conditioning and/or vent system for a few minutes before allowing a helmet to be rented again after each return.

3. The helmet cleaning, sanitation, and dispensing system of claim 1, wherein
   heat comes from vents under a helmet holding system, holding a helmet in place.

4. The helmet cleaning, sanitation, and dispensing system of claim 1, wherein
   each dispensing box has an individual cooling system;
   a modular case allows for unique shapes and replacement of an individual dispensing box in the event of any breakage inside.

5. The helmet cleaning, sanitation, and dispensing system of claim 1, wherein
   each box has an individual heating system.

6. The helmet cleaning, sanitation, and dispensing system of claim 1, wherein
   the individual boxes or rows of boxes are modular; and
   the individual boxes are further comprised of an individual heat system.

7. The helmet cleaning, sanitation, and dispensing system of claim 1, wherein
   one or more rows or boxes are added or removed from the helmet cleaning, sanitation, and dispensing system to expand or reduce an amount of available helmets.

8. The helmet cleaning, sanitation, and dispensing system of claim 1, wherein
   an interior of a based station supporting module is further comprised of a helmet pedestal.

9. The helmet cleaning, sanitation, and dispensing system of claim 1, further comprising
   one or more solar panels to produce all or a portion of an electrical need for the helmet cleaning, sanitation, and dispensing system.

10. The helmet cleaning, sanitation, and dispensing system of claim 1, further comprising
    an all-natural or chemical spray dispenser to sanitize a helmet.

11. The helmet cleaning, sanitation, and dispensing system of claim 1, wherein
    each box further comprised of a damaged button to press when a helmet is returned damaged to signal that the helmet cannot be rented until serviced; and
    individual boxes are disabled by a system software if an individual boxes heating or cooling system is non functional.

12. The helmet cleaning, sanitation, and dispensing system of claim 1, wherein a helmet is comprised of
    a replaceable outer shells, inner support and/or straps;
    a replaceable, thin outer shells are custom printed for replaceable design concepts, seasonal themes or sponsor marketing (logo and color) themes.

13. The helmet cleaning, sanitation, and dispensing system of claim 1, further comprising
    an app or application is used to let customers know what station has available helmets for rent and time left on a helmets rental;
    all stations will be connected throughout a city keeping track of helmet locations, availability, and usage;
    a credit card reader as well as a simple yearly key card or fob that customers can keep on keychain, pocket or wallet that is swiped and a helmet box is assigned rental service; and
    a video camera at the top to record transactions for safety.

14. The helmet of claim 13, further comprising
    one or more helmets with a built-in camera;
    the built in camera automatically starts recording when a helmet is put on and when the helmet is returned, a full video is uploaded to a server and sends a link to download or view the uploaded video.

15. The helmet cleaning, sanitation, and dispensing system of claim 1, wherein cleaning and sanitation for a helmet includes:
    a spray cleaner inside and out of helmet once placed in box instead of heat and then dried with forced air flow;
    an outside spray cleaner with wipe dispenser that is activated with every rental for extra cleaning or instead of heat or spraying inside box; or
    peel-able and replaceable inside layers of a helmet.

16. The helmet cleaning, sanitation, and dispensing system of claim 1, further comprising poles which would allow a helmet to slide on that suspends a helmet in air inside the same a box so it keeps the helmet hovering over the Heat, UV light, or any other cleaning lights and possibly steam and/or cleaner agent are used.

\* \* \* \* \*